United States Patent [19]
Miura et al.

[11] Patent Number: 5,777,158
[45] Date of Patent: Jul. 7, 1998

[54] NON-HYGROSCOPIC CRYSTALS OF P-AMINOMETHYLBENZOIC ACID AND PROCESS FOR PREPARING THE SAME

[75] Inventors: Motoo Miura; Hideo Miyata; Kohei Morikawa, all of Kanagawa, Japan

[73] Assignee: Showa Denko K.K., Tokyo, Japan

[21] Appl. No.: 917,688

[22] Filed: Aug. 26, 1997

[30]  Foreign Application Priority Data

Aug. 27, 1996 [JP] Japan .................................. 8-225397

[51] Int. Cl.$^6$ .................................................. C07C 229/00
[52] U.S. Cl. ........................................................ 562/442
[58] Field of Search ............................................ 562/442

[56]  References Cited

U.S. PATENT DOCUMENTS 3,859,342  1/1975  Fukumi et al. ........................ 562/442

FOREIGN PATENT DOCUMENTS 1929743  12/1969  Germany .

OTHER PUBLICATIONS

Database Caplus, DN 68:59307, (Kazmirowski et al., P-aminomethylbenzoic acid, East German patent DD 55034, Abstract), Apr. 5, 1967.

*Primary Examiner*—Gary Geist
*Assistant Examiner*—Brian J. Davis
*Attorney, Agent, or Firm*—Sughrue, Mion, Zinn, Macpeak & Seas, PLLC

[57]  ABSTRACT

The novel non-hygroscopic crystals of p-aminomethylbenzoic acid can be obtained by heating hygroscopic crystals of p-aminomethylbenzoic acid with keeping the hygroscopic crystals in contact with moisture to transit the hygroscopic crystals to non-hygroscopic crystals.

The non-hygroscopic crystals of p-aminomethylbenzoic acid can be particularly advantageously handled in the atmosphere as compared with the conventional hygroscopic crystals. Especially when the p-aminomethylbenzoic acid is used for the non-aqueous reaction, the crystals of the invention are exceptionally advantageous from the viewpoints of removal of moisture and humidity control.

2 Claims, 4 Drawing Sheets

1

NON-HYGROSCOPIC CRYSTALS OF P-AMINOMETHYLBENZOIC ACID AND PROCESS FOR PREPARING THE SAME

FIELD OF THE INVENTION

The present invention relates to novel crystals of p-aminomethylbenzoic acid, which have no hygroscopicity, and to a process for preparing the same.

BACKGROUND OF THE INVENTION

A p-aminomethylbenzoic acid is per se used as pharmaceutical, or used as a starting material or an intermediate product for preparing various agricultural chemicals, pharmaceuticals and other useful organic compounds.

The p-aminomethylbenzoic acid or its salts are prepared by, for example, the following processes.

(1) A p-cyanobenzoic acid is reduced in an aqueous solution of alkali using a ruthenium catalyst, as described in Japanese Patent Laid-Open Publication No. 32536/1976.

(2) A p-cyanobenzoic acid ester is heated in an aqueous solution of an alkali metal or an alkaline earth metal or in an aqueous solution of ammonia in the presence of hydrogen and a hydrogenation catalyst, as described in Japanese Patent Publication No. 23825/1978.

(3) A 4-hydroxyiminomethylbenzoic acid is reduced in an acid or a neutral aqueous solution using palladium and rhodium as a catalyst, as described in Japanese Patent Publication No. 17780/1985.

(4) 4-Cyanobenzylamine is hydrolyzed in an aqueous solution of alkali, as described in Izv. Akad. Nauk Kaz. SSR Ser., Khim, (1967), 17 (6), 82–4.

(5) A p-chloromethylbenzoic acid is aminated with ammonia in an aqueous solution, as described in German Patent No. 1,929,743.

The p-aminomethylbenzoic acid is generally handled in the form of crystals, and in the conventional processes, the crystals are obtained from a reaction solution containing the produced p-aminomethylbenzoic acid by means of neutralization crystallization or concentration crystallization. Thus far, hygroscopicity of the crystals obtained by those processes has not been discussed at all, so that analyses of the crystals obtained by the processes have been made. As a result, it has been confirmed that all of those crystals have hygroscopicity and they absorb 1 to 30% by weight of moisture based on the amount of the p-aminomethylbenzoic acid.

The moisture (or water) absorbed by the crystals can be removed by drying the crystals, but even if the moisture (or water) is removed, the crystals absorb atmospheric moisture again and return to moisture-containing crystals unless strict humidity control is conducted.

On that account, the conventional crystals of p-aminomethylbenzoic acid have serious problems in the removal of moisture and the humidity control. Especially when the p-aminomethylbenzoic acid is used for non-aqueous reaction, it is necessary to remove moisture prior to the reaction.

OBJECT OF THE INVENTION

It is, therefore, an object of the present invention to provide novel crystals of p-aminomethylbenzoic acid, which have no hygroscopicity, and to provide a process for preparing the novel crystals.

SUMMARY OF THE INVENTION

The present inventors have earnestly studied to solve such problems as described above, and as a result, they have prepared novel crystals (referred to as "α-type crystals" hereinafter) of p-aminomethylbenzoic acid, which are characterized by having no hygroscopicity.

DETAILED DESCRIPTION OF THE INVENTION

Figure 1:
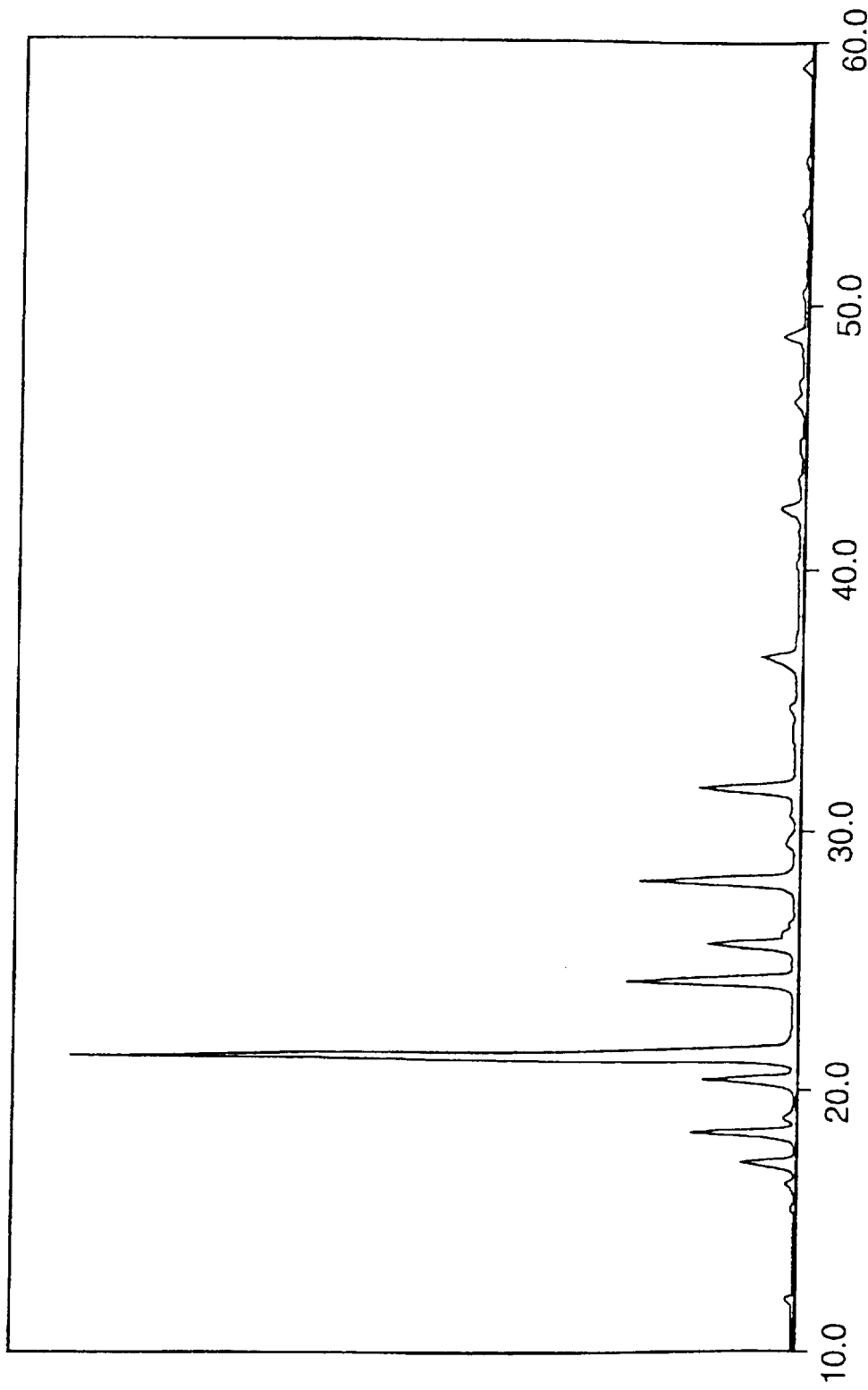
FIG. 1 shows XRD patterns of α-type crystals of p-aminomethylbenzoic acid according to the present invention, said crystals being obtained in Example 1.

The α-type crystals of p-aminomethylbenzoic acid according to the invention can be prepared by heating hygroscopic crystals of p-aminomethylbenzoic acid, which can be prepared in a conventional manner, with keeping the hygroscopic crystals in contact with moisture to transit the hygroscopic crystals to non-hygroscopic crystals.

The term "moisture" used herein includes water and drop of water.

In this process, the amount of moisture to be contacted is usually 1 to 100% by weight based on the amount of p-aminomethylbenzoic acid in the hygroscopic crystals, and the amount thereof is preferably 3 to 70% by weight, particularly preferably 5 to 50% by weight, from the viewpoints of transition rate, etc. In case of transiting moisture-containing hygroscopic crystals to non-hygroscopic crystals, addition of moisture is not necessarily performed, but in case of transiting dry hygroscopic crystals to non-hygroscopic crystals, moisture should be added in a necessary amount. It is preferable that the moisture is uniformly added by spraying. Also in case of hygroscopic crystals which have absorbed atmospheric moisture, addition of moisture is not necessarily performed, but it is advantageous to add moisture because the transition rate can be increased.

The contact of the hygroscopic crystals with the moisture can be conducted by, for example, putting the hygroscopic crystals in a humid atmosphere (steam).

In order to efficiently contact the hygroscopic crystals with the moisture, it is preferable to keep the hygroscopic crystals in the state of fluidizing under the humid atmosphere (steam). Especially, the hygroscopic crystals and the moisture are contacted efficiently by putting the hygroscopic crystals into a container kept at humid atmosphere therein, and rotating the container to fluidize the hygroscopic crystals, whereby the transition rate can be increased.

The temperature for the transition (environmental temperature) is preferably 60° to 200° C., and it is particularly preferably 90° to 150° C. from the viewpoints of transition rate and energy cost.

If the α-type crystals of the invention are added as seed crystals, the period of time for the transition can be shortened. In this case, the amount of the α-type crystals to be added is usually 0.01 to 100% by weight, preferably 0.1 to 50% by weight, based on the amount of the hygroscopic crystals.

Though the period of time for the transition greatly varies depending on the temperature for the transition, amount of the moisture, presence or absence of seed crystals, fluidity, etc., it is preferably 1 to 24 hours, particularly preferably 3 to 12 hours, because uniform α-type crystals can be obtained.

The α-type crystals of the invention obtained by the above process are non-hygroscopic and do not absorb atmospheric moisture under the conditions of ordinary temperature and humidity.

More specifically, the non-hygroscopic α-type crystals of the invention do not absorb moisture even when they are allowed to stand in the atmosphere for 12 hours, and the water absorption of the crystals after the crystals are allowed to stand for 24 hours under the conditions of a temperature of 40° C. and a relative humidity of 90% is not more than 5% by weight, preferably not more than 3% by weight, more preferably riot more than 1% by weight, particularly not more than 0.5% by weight.

The water absorption is given by the following formula:

$$\text{Water absorption (\%)} = \frac{\text{(weight after absorption)} - \text{(dry weight)}}{\text{dry weight}} \times 100$$

The non-hygroscopic α-type crystals of the invention may contain conventional hygroscopic p-aminomethylbenzoic acid crystal as far as that the water absorption is within the above range.

From the analytical data of X-ray diffractometry or infrared absorption spectrum, it can be ascertained that the non-hygroscopic α-type crystals of the invention are crystals of p-aminomethylbenzoic acid.

Figure 2:
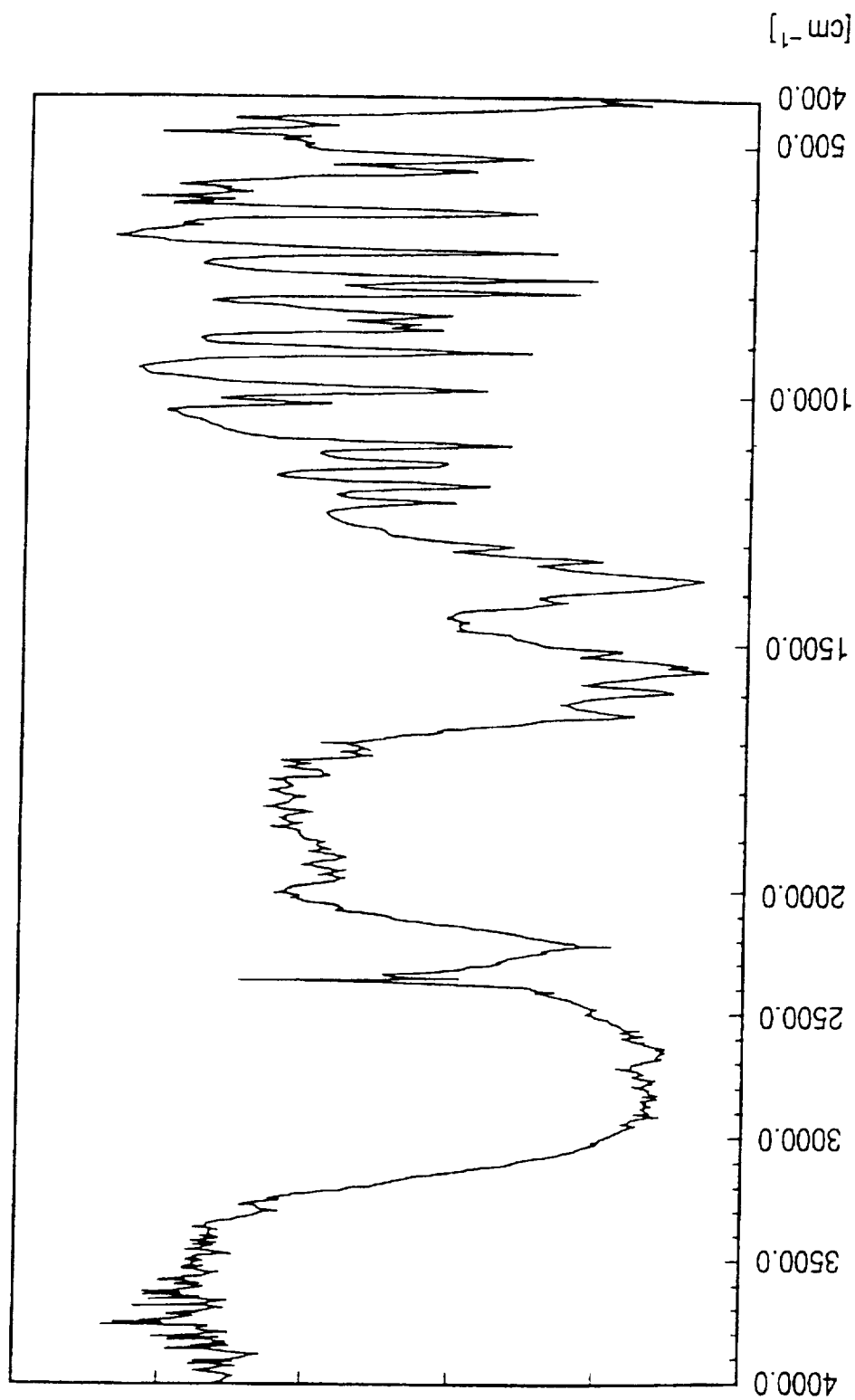
FIG. 2 shows an infrared absorption spectrum of α-type crystals of p-aminomethylbenzoic acid according to the present invention, said crystals being obtained in Example 1.
Figure 3:
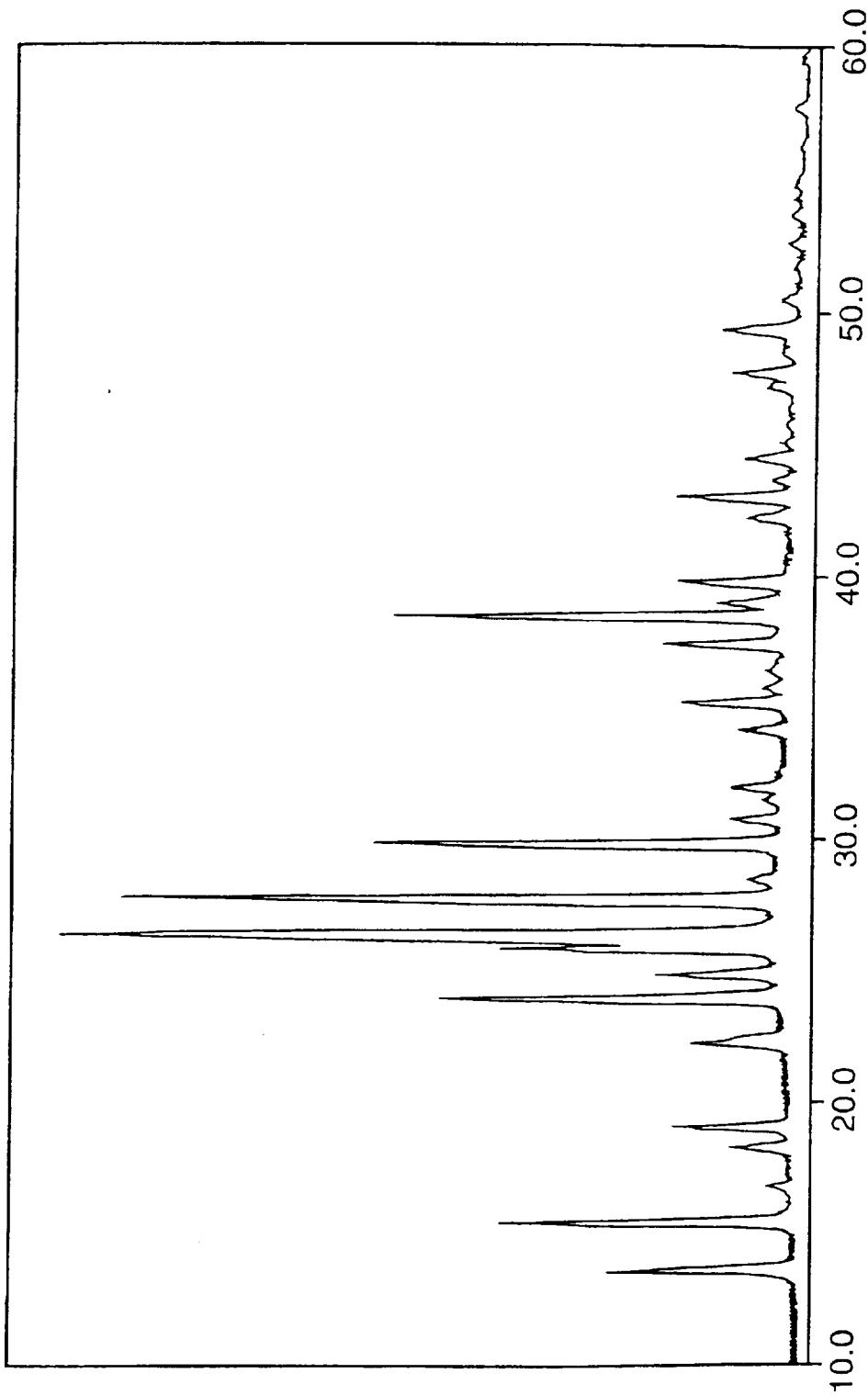
FIG. 3 shows XRD patterns of hygroscopic crystals of p-aminomethylbenzoic acid, said crystals being obtained in Reference Example 1.
Figure 4:
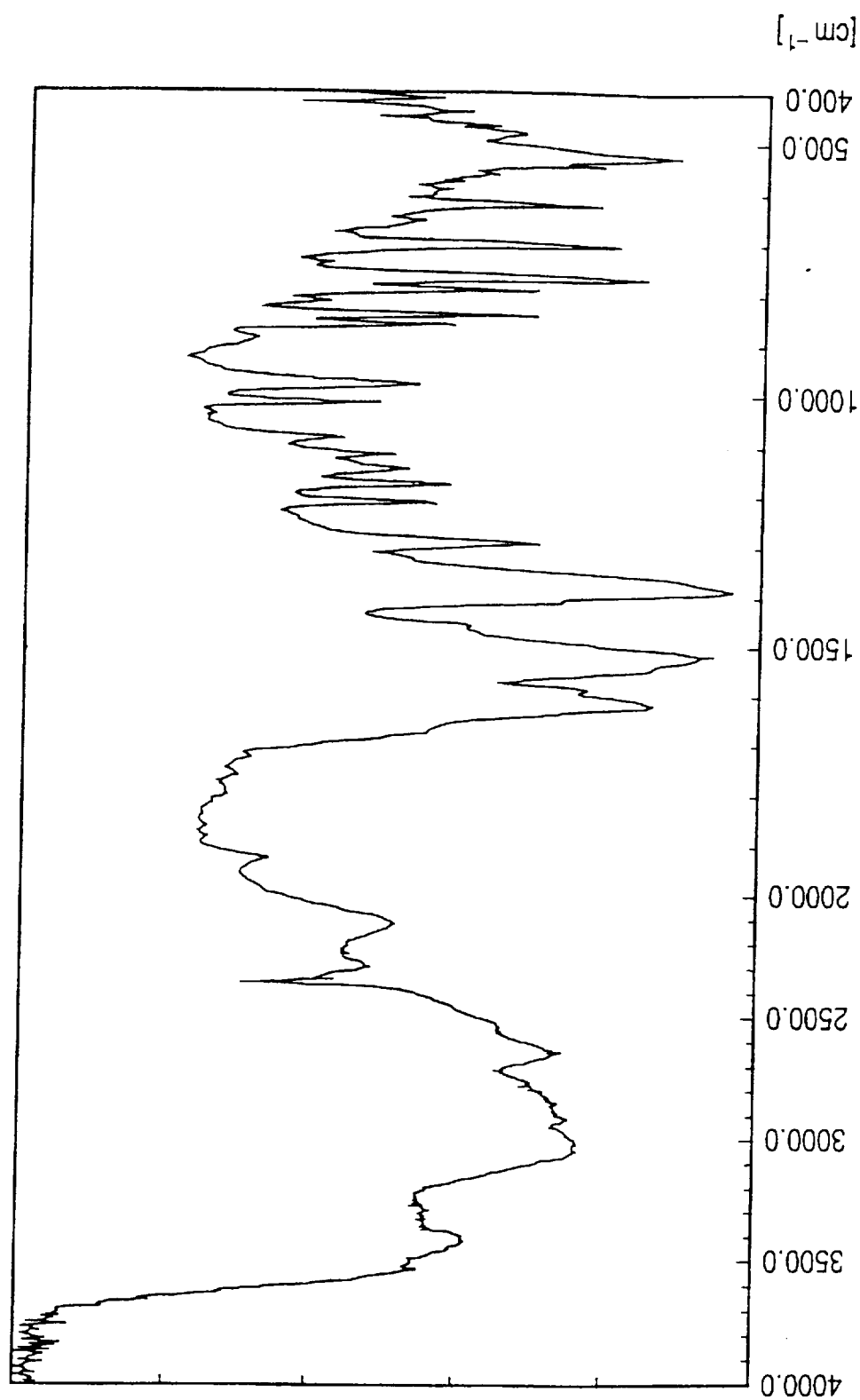
FIG. 4 shows an infrared absorption spectrum of hygroscopic crystals of p-aminomethylbenzoic acid, said crystals being obtained in Reference Example 1.

In particular, the non-hygroscopic α-type crystals of the invention exhibit characteristic peaks at the lattice spacing d=4.12 (±0.02), 3.64 (±0.02) and 3.17 (±0.02) in the X-ray diffractometry as shown in FIG. 1 and exhibit characteristic absorption at 914 (±5) cm$^{-1}$ in the infrared absorption spectrum as shown in FIG. 2, differently from conventional hygroscopic crystals which have absorbed moisture. The conventional hygroscopic crystals which have absorbed moisture exhibit characteristic peaks at the lattice spacing d=3.36 (±0.02), 3.19 (±0.02) and 2.98 (±0.02) in the X-ray diffractometry as shown in FIG. 3 and exhibit characteristic absorption at approx. 3,200–3,600 cm$^{-1}$ in the infrared absorption spectrum as shown in FIG. 4.

EFFECT OF THE INVENTION

The novel α-type crystals of p-aminomethylbenzoic acid provided by the present invention are characterized by being non-hygroscopic and by absorbing no atmospheric moisture. Therefore, the crystals can be particularly advantageously handled in the atmosphere as compared with the conventional hygroscopic crystals. Especially when the p-aminomethylbenzoic acid is used for the non-aqueous reaction, the crystals of the invention are exceptionally advantageous from the viewpoints of removal of moisture and humidity control.

EXAMPLE

The present invention will be further described with reference to the following examples, but it should be construed that the invention is in no way limited to those examples.

Example 1

35 Grams of 4-cyanobenzylamine was added to 160 g of an 8% aqueous solution of sodium hydroxide and hydrolyzed under reflux at 100° C. for 10 hours. After cooling, to the resulting solution was added sulfuric acid until pH of the solution became 7.2, whereby white crystals were precipitated. The white crystals were filtered to obtain 30 g of moisture-containing hygroscopic crystals of p-aminomethylbenzoic acid.

Lattice spacing d in X-ray diffractometry (CuKα, powder method)=3.36, 3.19, 2.98

Characteristic absorption in infrared absorption spectrum (FT-IR, KBr): 3,200–3,600 cm$^{-1}$ 30 Grams of the hygroscopic crystals (moisture content: 30%) of p-aminomethylbenzoic acid obtained above were introduced into a rotating vessel (rotating flask) equipped with condenser at top portion, and the vessel was rotated at a bath temperature of 130° C. for 6 hours under normal pressure to fluidize the crystals. Then, dry air was passed through the rotating vessel to remove moisture remaining in the vessel. Thus, 20.6 g of α-type crystals of p-aminomethylbenzoic acid were obtained.

The α-type crystals of p-aminomethylbenzoic acid were allowed to stand in the atmosphere (temperature: 25° C., relative humidity: 60%) for 12 hours, and the weight of the crystals was measured. As a result, the weight of the crystals was 20.6 g which was the same as that measured before the crystals were allowed to stand. Further, the moisture content in the crystals was measured by Karl Fischer coulometric titration method. As a result, the moisture content was lower than the limit of detection.

Conditions of Karl Fischer Method

In a closed vessel, 0.5 g of p-aminomethylbenzoic acid crystals were dissolved in 5.0 g of acetic acid (for non-aqueous titration, moisture content: not more than 500 ppm by weight), and the resulting solution was analyzed by means of Karl Fischer coulometric titration apparatus (available from Mitsubishi Chemical Co., Ltd.).

Lattice spacing d in X-ray diffractometry (CuKα, powder method)=4.12, 3.64, 3.17

Characteristic absorption in infrared absorption spectrum (FT-IR, KBr): 914 cm$^{-1}$

Reference Example 1

30 Grams of moisture-containing hygroscopic crystals (moisture content: 30%) of p-aminomethylbenzoic acid prepared in the same manner as in Example 1 were dried by passing dry air at room temperature for 24 hours, to obtain 22.5 g of crystals of p-aminomethylbenzoic acid. The crystals thus obtained were not α-type crystals and they were hygroscopic. After the crystals of p-aminomethylbenzoic acid were allowed to stand in the atmosphere (temperature 25° C., relative humidity: 60%) for 12 hours, the weight of the crystals was measured. As a result, the weight of the crystals was 23.2 g. Further, the moisture content in the crystals was measured by Karl Fischer coulometric titration method. As a result, the moisture content was 10%.

Lattice spacing d in X-ray diffractometry (CuKα, powder method)=3.36, 3.19, 2.98

Characteristic absorption in infrared absorption spectrum (FT-IR, KBr): 3,200–3,600 cm$^{-1}$

Reference Example 2

30 Grams of moisture-containing hygroscopic crystal (moisture content: 30%) of p-aminomethylbenzoic acid pre pared in the same manner as in Example 1 were dried at a bath temperature of 130° C. for 4 hours under reduced pressure (10 mmHg), to obtain 20.6 g of crystals of p-aminomethylbenzoic acid. The dried hygroscopic crystals of p-aminomethylbenzoic acid thus obtained were introduced into a rotating vessel (rotating flask) equipped with condenser at top portion, and the vessel was rotated at a bath temperature of 130° C. for 6 hours under normal pressure to fluidize the crystals. Thus, 20.6 g of crystals of p-aminomethylbenzoic acid were obtained. The crystals thus obtained were not α-type crystals and they were still hygroscopic. After the crystals were allowed to stand in the atmosphere (temperature: 25° C., relative humidity: 60%) for 12 hours, the weight of the crystals was measured. As a result, the weight of the crystals was 22.5 g. Further, the moisture content in the crystals was measured by Karl Fischer coulometric titration method. As a result, the moisture content was 8.6%.

Example 2

30 Grams of moisture-containing hygroscopic crystals (moisture content: 30%) of p-aminomethylbenzoic acid prepared in the same manner as in Example 1 were introduced into a rotating vessel (rotating flask) equipped with condenser at top portion, and the vessel was rotated at a bath temperature of 120° C. for 10 hours under normal pressure to fluidize the crystals. Then, dry air was passed through the rotating vessel to remove moisture remaining in the vessel. Thus, 20.7 g of α-type crystals of p-aminomethylbenzoic acid were obtained.

After the α-type crystals of p-aminomethylbenzoic acid were allowed to stand in the atmosphere (temperature: 25° C., relative humidity: 60%) for 12 hours, the weight of the crystals was measured. As a result, the weight of the crystals was 20.7 g which was the same as that measured before the crystals were allowed to stand. Further, the moisture content in the crystals was measured by Karl Fischer coulometric titration method. As a result, the moisture content was lower than the limit of detection.

Example 3

30 Grams of moisture-containing hygroscopic crystals (moisture content: 30%) of p-aminomethylbenzoic acid prepared in the same manner as in Example 1 were dried in the same manner as in Reference Example 2, to obtain 20.7 g of hygroscopic crystals of p-aminomethylbenzoic acid. The hygroscopic crystals of p-aminomethylbenzoic acid thus obtained were introduced into a rotating vessel (rotating flask) equipped with condenser at top portion, and the vessel was rotated at a bath temperature of 130° C. for 6 hours under normal pressure to fluidize the crystals, while the crystals were sprayed with 10 g of water by means of a spray. Then, dry air was passed through the rotating vessel to remove moisture remaining in the vessel. Thus, 20.4 g of α-type crystals of p-aminomethylbenzoic acid were obtained.

After the α-type crystals of p-aminomethylbenzoic acid were allowed to stand in the atmosphere (temperature: 25° C., relative humidity: 60%) for 12 hours, the weight of the crystals was measured. As a result, the weight of the crystals was 20.6 g which was substantially the same as that measured before the crystals were allowed to stand.

Further, the moisture content in the crystals was measured by Karl Fischer coulometric titration method. As a result, the moisture content was lower than the limit of detection.

Example 4

30 Grams of moisture-containing hygroscopic crystals (moisture content: 30%) of p-aminomethylbenzoic acid prepared in the same manner as in Example 1 were introduced into a rotating vessel (rotating flask) equipped with condenser at top portion together with 3 g of α-type crystals of p-aminomethylbenzoic acid, and the vessel was rotated at a bath temperature of 130° C. for 4 hours under normal pressure to fluidize the crystals. Then, dry air was passed through the rotating vessel to remove moisture remaining in the vessel. Thus, 23.6 g of α-type crystals of p-aminomethylbenzoic acid were obtained.

After the α-type crystals of p-aminomethylbenzoic acid were allowed to stand in the atmosphere (temperature: 25° C., relative humidity: 60%) for 12 hours, the weight of the crystals was measured. As a result, the weight of the crystals was 23.6 g which was the same as that measured before the crystals were allowed to stand. Further, the moisture content in the crystals was measured by Karl Fischer coulometric titration method. As a result, the moisture content was lower than the limit of detection.

Example 5

35 Grams of 4-cyanobenzoic acid and 15 grams of Ru/C were added to 130 g of an 8% aqueous solution of sodium hydroxide and the hydrogen-reduction was conducted in an autoclave under a hydrogen pressure of 30 kg/cm$^2$ at 120° C. for 3 hours. After cooling the reaction liquid, the catalyst was filtrated, and to the filtrate, was added sulfuric acid until pH of the filtrate became 7.2, whereby white crystals were precipitated. The white crystals were filtered to obtain 28 g of moisture-containing hygroscopic crystals of p-aminomethylbenzoic acid.

28 Grams of moisture-containing hygroscopic crystals (moisture content: 20%) of p-aminomethylbenzoic acid thus obtained were heated with keeping the hygroscopic crystals in contact with moisture in the same manner as in Example 1. As a result, 22.4 g of α-type crystals of p-aminomethylbenzoic acid which were the same as obtained in Example 1 were obtained.

What is claimed is:

1. Non-hygroscopic crystals of p-aminomethylbenzoic acid.

2. A process for preparing non-hygroscopic crystals of p-aminomethylbenzoic acid, comprising heating hygroscopic crystals of p-aminomethylbenzoic acid with keeping the hygroscopic crystals in contact with moisture to transit the hygroscopic crystals to non-hygroscopic crystals.

* * * * *